US010314182B2

(12) United States Patent
Teng et al.

(10) Patent No.: US 10,314,182 B2
(45) Date of Patent: Jun. 4, 2019

(54) MAGNETICALLY HELD DIAPER MONITOR

(71) Applicant: SHENZHEN HYAN MICROELECTRONICS CO., LTD., Shenzhen, Guangdong (CN)

(72) Inventors: Yujie Teng, Guangdong (CN); Yudong Teng, Guangdong (CN); Da Teng, Guangdong (CN)

(73) Assignee: SHENZNEHN HYAN MICROELECTRONICS CO., LTD., Guangdong (CN)

( * ) Notice: Subject to any disclaimer, the term of this patent is extended or adjusted under 35 U.S.C. 154(b) by 225 days.

(21) Appl. No.: 15/394,987

(22) Filed: Dec. 30, 2016

(65) Prior Publication Data
US 2017/0325345 A1    Nov. 9, 2017

(30) Foreign Application Priority Data

May 6, 2016    (CN) .......................... 2016 1 0296882

(51) Int. Cl.
| *A61F 13/84* | (2006.01) |
| *H05K 5/00* | (2006.01) |
| *G01D 11/30* | (2006.01) |
| *H01R 13/62* | (2006.01) |
| *H05K 5/02* | (2006.01) |
| *A61F 13/505* | (2006.01) |

(Continued)

(52) U.S. Cl.
CPC ........... *H05K 5/0047* (2013.01); *A61B 5/202* (2013.01); *A61B 5/6808* (2013.01); *A61B 5/6879* (2013.01); *A61F 13/42* (2013.01); *A61F 13/505* (2013.01); *A61F 13/84* (2013.01); *G01D 11/30* (2013.01); *H01R 13/6205* (2013.01); *H05K 5/0217* (2013.01); *A61B 2503/04* (2013.01); *A61B 2560/0204* (2013.01); *A61B 2562/225* (2013.01); *A61F 2013/8479* (2013.01); *A61F 2013/8488* (2013.01)

(58) Field of Classification Search
CPC .. H01R 13/6205; G01D 11/30; H05K 5/0217; A61F 13/84; A61F 2013/8488; A61F 2013/8479
USPC ....... 73/866.5, 53.01, 64.56, 865.8; 340/603, 340/604; 604/358–402
See application file for complete search history.

(56) References Cited

U.S. PATENT DOCUMENTS

| 7,250,547 | B1* | 7/2007 | Hofmeister | ............. | A61F 13/42 340/573.5 |
| 2014/0262774 | A1* | 9/2014 | Bhatia | .................... | G01N 27/07 204/403.01 |

* cited by examiner

Primary Examiner — Robert R Raevis
(74) Attorney, Agent, or Firm — Jackson IPG PLLC; Demian K. Jackson

(57) ABSTRACT

A magnetically held diaper monitor comprises a power supply part and a control part. The power supply part comprises a lower shell, and a battery and a power circuit board embedded in the lower shell. The power circuit board is provided with a plurality of lower magnetic electrodes and two lower magnetic terminals. The control part comprises an upper shell and a control circuit board embedded in the upper shell. The control circuit board is provided with upper magnetic electrodes which are in one-to-one correspondence to the lower magnetic electrodes, and upper magnetic terminals which correspond to the lower magnetic terminals. A diaper sensor is clamped between the power supply part and the control part which are combined into a whole by attraction by means of a magnetic force and is connected to the control part via the magnetic electrodes. The control part obtains a power supply via the magnetic terminals.

9 Claims, 3 Drawing Sheets

(51) Int. Cl.
*A61B 5/00* (2006.01)
*A61F 13/42* (2006.01)
*A61B 5/20* (2006.01)

MAGNETICALLY HELD DIAPER MONITOR

FIELD OF THE INVENTION

The present invention relates to an intelligent diaper, in particular to a magnetically held diaper monitor for an intelligent diaper.

BACKGROUND OF THE INVENTION

The paper diapers and panty-shape diapers (hereinafter referred to as diapers) are used as daily necessities frequently used by infants and the aged. However, it is unavailable for a traditional diaper to judge whether or not a wearer has urinated or defecated from the appearance, a caregiver needs to observe the diaper frequently, and therefore, the wearer will often feel uncomfortable because the diaper is not changed timely.

Because some diapers are provided with sensors and alarm circuits, the caregiver may be reminded by an alarm signal sent after the wearer urinates or defecates, to clear and replace the diaper in time. But the alarm circuit part has higher cost and is combined with the diaper as disposable goods, and accordingly, the use cost is very high; cleaning and sterilization will be involved in the event that the alarm circuit part is repeatedly used, thereby being very inconvenient. To solve said problem, an improvement scheme in which a diaper sensor and a circuit part are designed separately, the sensor and the diaper are combined as a disposable part, and the sensor and the alarm circuit part are connected in a traditional pluggable connection manner is performed, such that the circuit part having higher cost can be used repeatedly. But, because the diaper sensor generally adopts a cloth substrate or a paper substrate, and is strip-shaped integrally, has a thickness less than 1 mm and is likely to bend, the defects of difficulty and unreliability in connection are caused due to the adoption of the traditional pluggable connection manner. Meanwhile, the diaper sensor is connected with the alarm circuit part in a pluggable connection manner, and then the alarm circuit part is directly provided with a button battery, thereby bringing difficulty to a waterproof design of an alarm product.

SUMMARY OF THE INVENTION

To solve said defects existing in connection of a split diaper sensor and alarm product in the prior art, the present invention provides a magnetically held diaper monitor in which a split structure design is adopted to a control part, a power supply part and a sensor capable of being adhered to a diaper. The diaper sensor is clamped between the power supply part and the control part which are combined into a whole by attraction by means of a magnetic force, and reliable connection and power supply can be realized.

According to the diaper monitor of the present invention, a split design scheme is adopted to the control part, the power supply part and the diaper sensor capable of being adhered to or built in the diaper. The power supply part and the control part between which the diaper sensor is tightly clamped are combined into a whole by attraction by means of the magnetic force via symmetrically configured magnetic electrodes and magnetic terminals. Conductive connecting parts of the diaper sensor are tightly crimped by the symmetrically configured magnetic electrodes to realize reliable connection with a circuit of the control part. The control part obtains a direct-current power supply from the power supply part through direct contact among the symmetrically configured magnetic terminals. Here, the magnetic electrodes refer to magnetic conductors, and meanwhile may be used as connecting electrodes and magnets. The magnetic terminals (or magnetic power supply terminals) refer to magnetic conductors, and meanwhile may be used as power supply terminals and magnets. The definitions of the magnetic electrodes and the magnetic terminals are applicable to the full text of the present invention.

The magnetically held diaper monitor of the present invention comprises a control part and a power supply part;

the power supply part comprises a lower shell having two positioning blind holes, a button battery and a power circuit board, wherein the button battery and the power circuit board are embedded in the lower shell through an insert injection molding process; a plurality of lower magnetic electrodes and two lower magnetic terminals are arranged at one end of the power circuit board, and the lower magnetic terminals and the lower magnetic electrodes penetrate out of a surface, where the positioning blind holes are located, of the lower shell;

the control part comprises an upper shell having two positioning pins and a control circuit board embedded in the shell through an insert injection molding process; upper magnetic electrodes which are in one-to-one correspondence to the lower magnetic electrodes and two upper magnetic terminals which correspond to the two lower magnetic terminals are arranged at one end of the control circuit board, and the upper magnetic terminals and the upper magnetic electrodes penetrate out of a surface, where the positioning pins are located, of the upper shell;

the diaper sensor is clamped between the power supply part and the control part which are combined with into a whole by attraction via the lower magnetic electrodes, the lower magnetic terminals and the corresponding upper magnetic electrodes and upper magnetic terminals; and, conductive connecting parts of the diaper sensor can be tightly crimped by the lower magnetic electrodes and the upper magnetic electrodes to realize reliable connection with the control circuit board; the lower magnetic terminals directly contact the upper magnetic terminals, such that the control circuit board obtains a direct-current power supply from the power supply part.

In a preferred embodiment, three lower magnetic electrodes are arranged on the power circuit board; three upper magnetic electrodes are arranged on the control circuit board; correspondingly, the diaper sensor also has three conductive connecting parts and positioning holes.

The power supply part, the diaper sensor and the control part are at a combined state, and the two positioning pins penetrating through the positioning holes in the diaper sensor are inserted into two positioning blind holes in the lower shell respectively to realize accurate positioning of the power supply part, the diaper sensor and the control part.

In the monitor, the lower magnetic electrodes, the lower magnetic terminals, the upper magnetic electrodes and the upper magnetic terminals are made from a magnetizable conducting material, for example, NdFeB, etc.

During implementation, the lower magnetic electrodes, the upper magnetic electrodes, the lower magnetic terminals and the upper magnetic terminals are cylindrical. It is available to adopt commercially available finished-product magnetic electrodes, magnetic terminals, etc. The magnetic electrodes and magnetic power supply terminals may also be fabricated by fixing (welding, for instance) formed green bodies of the magnetic electrodes and formed green bodies of the magnetic terminals onto a power circuit board or a control circuit board in advance, and then magnetizing.

According to the magnetically held diaper monitor of the present invention, a split design scheme is adopted to the power supply part, the control part and the diaper sensor. The power supply part and the control part between which the diaper sensor can be clamped conveniently are combined into a whole by attraction by means of a magnetic force of multiple pairs of symmetrically configured magnetic electrodes and magnetic terminals. Conductive connecting parts of the diaper sensor are tightly crimped by the multiple pairs of magnetic electrodes to realize reliable connection with a circuit of the control part. The control part obtains a direct-current power supply from the power supply part by the magnetic terminals which are in direct contact.

As an independent component, the power supply part can be recycled conveniently after the battery is exhausted; the control part having high cost can be reused to save the cost, and the disposable diaper sensor and the monitor are convenient to assemble and disassemble.

Because the power part and the control part are independent components, the button battery and the power circuit board are embedded and sealed in the lower shell through the insert injection molding process, and the control circuit board is embedded and sealed in the upper shell through the insert injection molding process, waterproof and moisture-proof effects are achieved to facilitate to protect the circuit part and the battery and prolong the service life thereof.

BRIEF DESCRIPTION OF THE DRAWINGS

FIGS. 3-5 are structural schematic drawings of the power supply part 1 in FIG. 1, wherein FIG. 3 is a stereogram, FIG. 4 is a front view, and FIG. 5 is a side view; and FIGS. 6-9 are structural schematic drawings of the control part 2 in FIG. 1, wherein FIG. 6 is a stereogram, FIG. 7 is a front view, FIG. 8 is a side view, and FIG. 9 is a vertical view.

DETAILED DESCRIPTION OF THE PREFERRED EMBODIMENTS

The present invention will be further illustrated below in conjunction with the drawings and embodiments.

Figure 1:
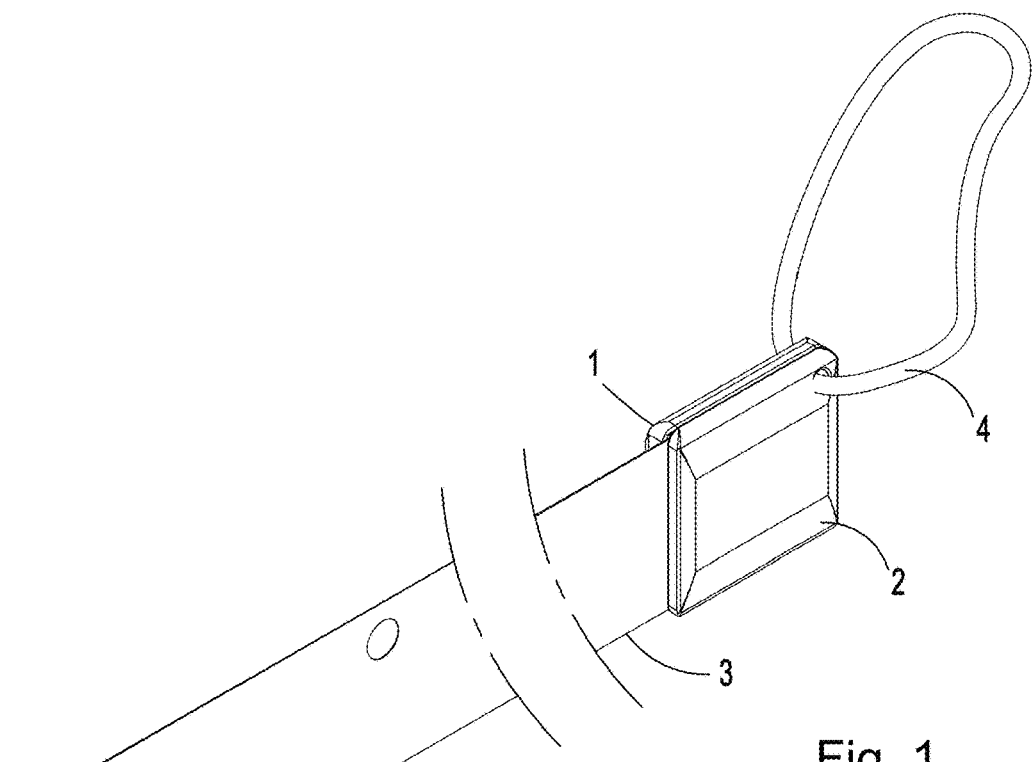
FIG. 1 is a structural schematic drawing of one embodiment of the diaper monitor of the present invention, wherein a diaper sensor 3 is clamped between a power supply part 1 and a control part 2.
Figure 2:
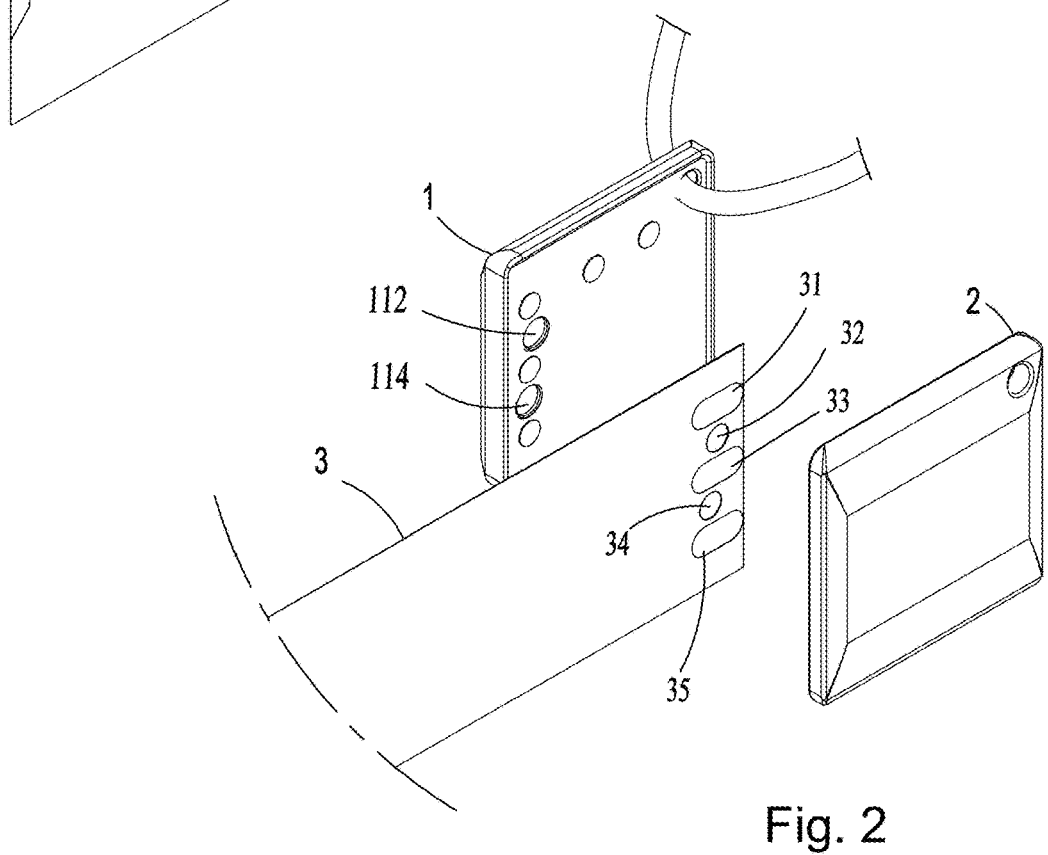
FIG. 2 is an exploded view of FIG. 1.

Referring to FIG. 1 and FIG. 2, the magnetically held diaper monitor of this embodiment mainly comprises a control part 2 and a power supply part 1. A split design is adopted to the control part 2, the power supply part 1 and a diaper sensor 3 capable of being attached to a diaper, wherein the power supply part 1 and the control part 2 between which a diaper sensor 3 can be clamped tightly are combined into a whole by attraction by means of an appropriate magnetic force via symmetrically configured magnetic electrodes and magnetic terminals; in addition, conductive connecting parts of the diaper sensor 3 are tightly crimped by the symmetrically configured magnetic electrodes to realize reliable connection with a circuit of the control part, and the control part 2 obtains a direct-current power supply from the power supply part 1 via direct contact among the symmetrically configured magnetic terminals.

Figure 3:
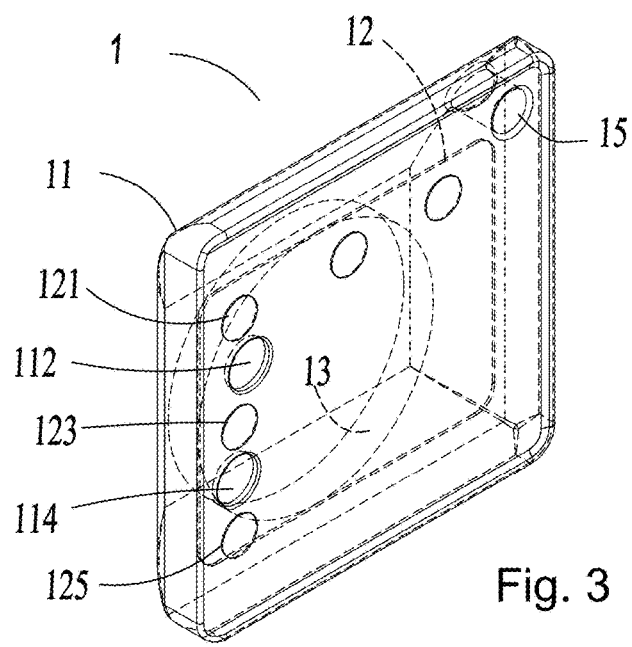
Figure 4:
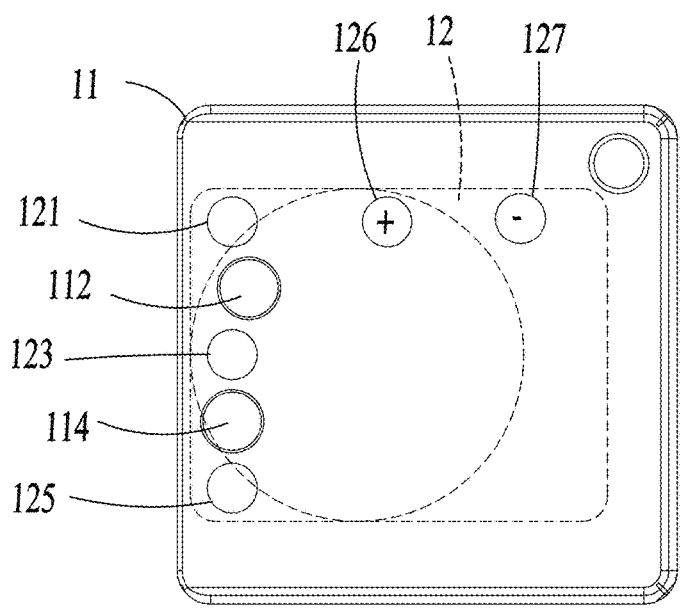
Figure 5:
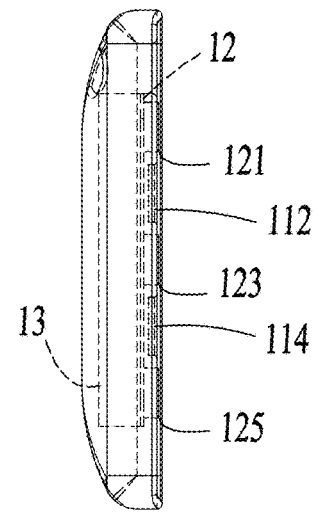
Figure 6:
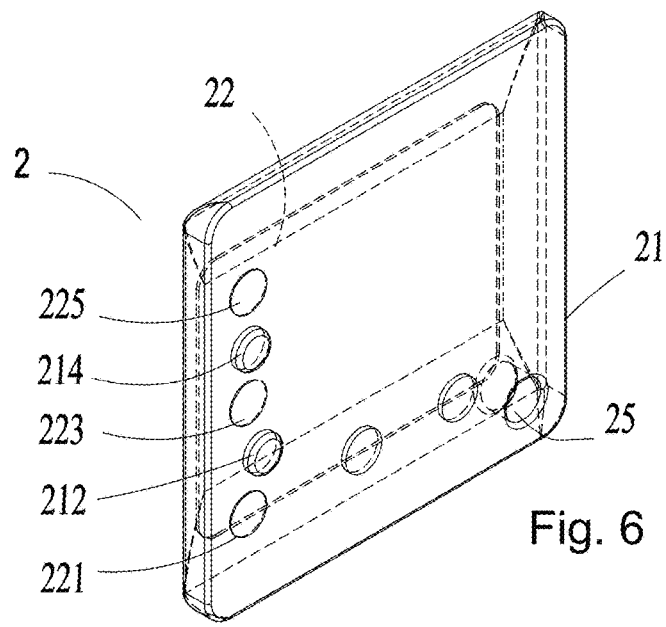
Figure 9:
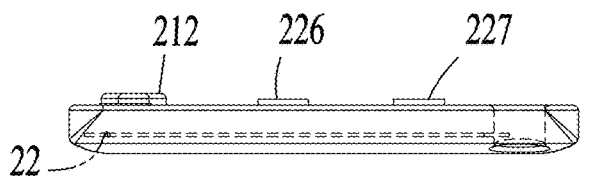
Figure 7:
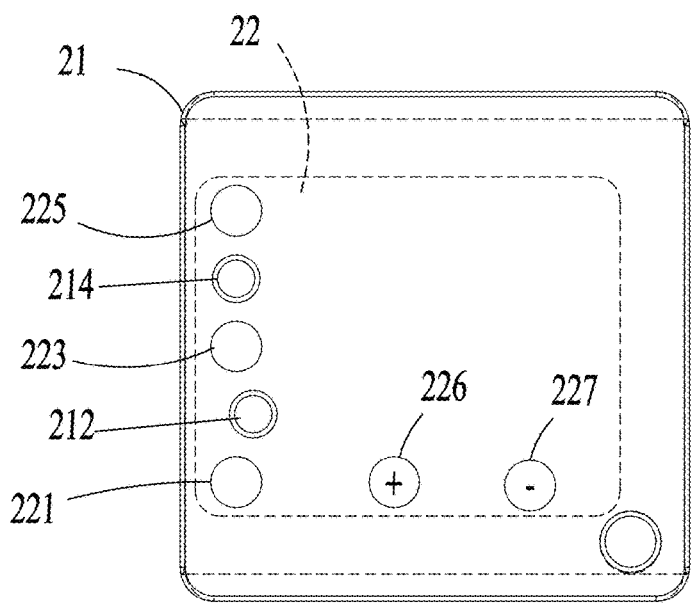
Figure 8:
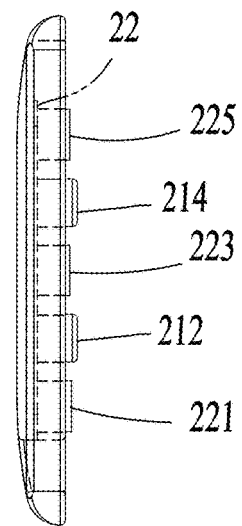

FIGS. 3-5 are structural schematic drawings of the power supply part 1. The power supply part 1 comprises a lower shell 11 having two positioning blind holes 112 and 114, a power circuit board 12 and a button battery 13; the power circuit board 12 and the button battery 13 are embedded in the lower shell 11 through an insert injection molding process, and the button battery 13 is located on the back of the power circuit board 12 and is welded to a printed power line on the power circuit board 12.

Three lower magnetic electrodes 121, 123 and 125 are arranged at the left end of the power circuit board 12, and two lower magnetic terminals 126 and 127 are welded to the upper edge of the power circuit board 12. The lower magnetic terminals and the lower magnetic electrodes penetrate out of a surface, where the positioning blind holes are located, of the lower shell 11, wherein all the penetrating ends are N poles. In FIGS. 3-5, the positioning blind hole 112 is located between the lower magnetic electrodes 121 and 123, and the positioning blind hole 114 is located between the lower magnetic electrodes 123 and 125. The two positioning blind holes 112 and 114 are asymmetrically configured to distinguish the front surface and the back surface of the diaper sensor. The lower magnetic terminals 126 and 127 are welded to a positive output end and a negative output end of the printed power line on the power circuit board 12 respectively.

FIGS. 6-9 are structural schematic drawings of the control part 2. The control part 2 comprises an upper shell 21 having two positioning pins 212 and 214, and a control circuit board 22 embedded in the upper shell 21 through an insert injection molding process. Upper magnetic electrodes 221, 223 and 225 which are in one-to-one correspondence to the lower magnetic electrodes 121, 123 and 125 and two upper magnetic terminals 226 and 227 which correspond to the two lower magnetic terminals 126 and 127 are arranged at one end, corresponding to the power circuit board 12, of the control circuit board 22. The upper magnetic terminals and the upper magnetic electrodes penetrate out of a surface, where the positioning pins (212 and 214) are located, of the upper shell 21, wherein all the penetrating ends are S poles. The two positioning pins 212 and 214 are also asymmetrically arranged, correspond to the two positioning blind holes 112 and 114 in the lower shell 11 respectively in position and are used for assembling and positioning the power supply part 1, the diaper sensor 3 and the control part 2 to ensure that the diaper sensor 3 is assembled at the correct side.

The upper magnetic terminals 226 and 227 are welded to a positive output end and a negative output end of the printed power line on the control circuit board 22 respectively. Here, the upper magnetic terminals 226 and 227 and the lower magnetic terminals 126 and 127 are combined by attraction by means of an appropriate magnetic force and directly contact to play a role of magnetizing a power supply switch, and the direct-current power supply of the power supply part 1 is connected to the control circuit board 22.

A new design or a traditional control circuit may also be available for the control circuit part with the control circuit board 22 as a carrier. The control circuit comprises a MCU, a detection unit connected to an input end of the MCU, a monitoring circuit connected to an output end of the MCU, etc. After a signal from the diaper sensor 3 is processed by the detection unit, the MCU judges whether a wearer has urinated or defecated and distinguishes feces from urine. The upper magnetic electrodes 221, 223 and 225 are respectively welded to three sensor signal input ends arranged on the control circuit board 22, and these sensor signal input ends are connected with an input of the detection unit.

When the power supply part 1, the diaper sensor 3 and the control part 2 are combined into a whole by attraction by means of the magnetic force, conductive connecting parts 31, 33 and 35 of the diaper sensor 3 (referring to FIG. 2) are tightly crimped by three groups of corresponding magnetic electrodes (namely the upper magnetic electrode 221 and the lower magnetic electrode 121, the upper magnetic electrode 223 and the lower magnetic electrode 123, and the upper magnetic electrode 225 and the lower magnetic electrode 125) respectively, such that reliable connection between the diaper sensor 3 and the input end of the detection unit is realized via the upper magnetic electrodes 221, 223 and 225.

For convenience in use, a lower through hole 15 may be arranged at one corner, away from the lower magnetic electrodes, of the lower shell 11; an upper through hole 25 which corresponds to the lower through hole 15 may be arranged at one corner, away from the upper magnetic electrodes, of the upper shell 21; a lacing 4 is threaded into the lower through hole and the upper through hole, such that the power supply part 1 and the control part 2 are combined into whole to avoid a baby from eating by mistake. The power supply part 1 can be replaced conveniently after the electric quantity is exhausted, by means of the connection of the lacing 4. A rope ring may also be arranged on the power supply part 1 and the control part 2 respectively to facilitate connection.

Referring to FIG. 2 and FIG. 1 for assembly of the product, positioning holes 32 and 34 in a connecting end of the diaper sensor 3 are aligned to positioning blind holes 112 and 114 (the power supply part 1) in the lower shell 11, such that the positioning pins 212 and 214 (the control part 1) on the upper shell 21 penetrate through the positioning holes 32 and 34 and inserted into the positioning blind holes to be positioned. The power supply part 1, the diaper sensor 3 and the control part 2 are combined into a whole by attraction by means of the magnetic force. The power supply part 1, the diaper sensor 3 and the control part 2 are at a combined state (FIG. 1), and conductive connecting parts 31, 33 and 35 of the diaper sensor 3 are tightly crimped by the three groups of magnetic electrodes respectively, and reliable connection between the diaper sensor 3 and the input end of the detection unit is realized via the upper magnetic electrodes 221, 223 and 225. Meanwhile, the upper magnetic terminals 226 and 227 and the lower magnetic terminals 126 and 127 are combined by attraction by means of a magnetic force and directly contact, and the direct-current power supply of the power supply part 1 is connected to the control circuit board 22.

When there is a need to dissemble the diaper sensor 3, an external force is applied to overcome an attractive magnetic force between the upper and lower magnetic electrodes and between the upper and lower magnetic terminals, such that the power supply part 1 and the control part 2 are separated quickly to replace the diaper sensor 3.

The monitor may be in use with a flexible diaper sensor having a cloth substrate or a paper substrate, etc. The structure, principle and use of the diaper sensor may refer to the patent description (No. CN201520516761.2). The diaper sensor should have three detection electrodes preferably to detect whether a wearer has urinated or defecated and distinguish feces from urine.

In the monitor, the lower magnetic electrodes, the lower magnetic terminals, the upper magnetic electrodes and the upper magnetic terminals are made from a magnetizable conducting material, for example, NdFeB, etc. Duration implementation, the magnetic electrodes and the magnetic power supply terminals may also be fabricated by fixing (welding, for instance) formed green bodies of the magnetic electrodes and formed green bodies of the magnetic terminals to a power circuit board or a control circuit board in advance, and then magnetizing.

The present invention is elaborated above according to the specific embodiments, but these detailed descriptions may not be interpreted to limit the content of these embodiments merely. Any improvements and equivalent alternative solutions made by those skilled in the art according to the concept and these descriptions of the present invention and in conjunction with the common general knowledge in the art should fall into the protection scope of claims of the present invention.

What is claimed is:

1. A magnetically held diaper monitor, comprising a control part; wherein, the magnetically held diaper monitor further comprises:
    a power supply part which comprises a lower shell having two positioning blind holes, and a power circuit board and a button battery which are embedded in the lower shell, wherein a plurality of lower magnetic electrodes and two lower magnetic terminals are arranged at one end of the power circuit board, and the lower magnetic terminals and the lower magnetic electrodes penetrate out of a surface, where positioning blind holes are located, of the lower shell;
    the control part comprises an upper shell having two positioning pins and a control circuit board embedded in the upper shell, wherein upper magnetic electrodes which are in one-to-one correspondence to the lower magnetic electrodes and two upper magnetic terminals which correspond to the two lower magnetic terminals are arranged at one end of the control circuit board, and the upper magnetic terminals and the upper magnetic electrodes protrude out of a surface, where the positioning pins are located, of the upper shell;
    the diaper sensor is clamped between the power supply part and the control part which are combined into a whole by attraction via the lower magnetic electrodes, the lower magnetic terminals and the corresponding upper magnetic electrodes and upper magnetic terminals; and, conductive connecting parts of the diaper sensor can be tightly crimped by the upper magnetic electrodes and the lower magnetic electrodes to realize reliable connection with the control circuit board, and the lower magnetic terminals directly contact the upper magnetic terminals, such that the control circuit board obtains a power supply from the power supply part.

2. The diaper monitor according to claim 1, wherein three lower magnetic electrodes are arranged on the power circuit board; three upper magnetic electrodes are arranged on the control circuit board.

3. The diaper monitor according to claim 1, wherein the power supply part, the diaper sensor and the control part are at a combined state, and the two positioning pins penetrating through positioning holes in the diaper sensor are inserted into the two positioning blind holes respectively.

4. The diaper monitor according to claim 1, wherein the power circuit board and the button battery are embedded in the lower shell through an insert injection molding process; the control circuit board is embedded into the upper shell through an insert injection molding process.

5. The diaper monitor according to claim 1, wherein the lower magnetic electrodes and the two lower magnetic terminals are formed by fixing formed green bodies onto the power circuit board in advance and then magnetizing; the upper magnetic electrodes and the two upper magnetic terminals are formed by fixing formed green bodies onto the control circuit board in advance and then magnetizing.

6. The diaper monitor according to claim 1, wherein the lower magnetic electrodes, the lower magnetic terminals, the upper magnetic electrodes and the upper magnetic terminals are made from a magnetizable conducting material.

7. The diaper monitor according to claim 1, wherein the lower magnetic electrodes, the upper magnetic electrodes, the lower magnetic terminals and the upper magnetic terminals are cylindrical.

8. The diaper monitor according to claim 1, wherein a lower through hole is arranged at one corner, away from the lower magnetic electrodes, of the lower shell; an upper through hole which corresponds to the lower through hole, is arranged at one corner, away from the upper magnetic electrodes, of the upper shell.

9. The diaper monitor according to claim 8, wherein a lacing is threaded into the lower through hole and the upper through hole.

* * * * *